(12) United States Patent
Maile et al.

(10) Patent No.: US 8,478,404 B2
(45) Date of Patent: Jul. 2, 2013

(54) OUTPUT CIRCUIT FOR BOTH CARDIAC CONTRACTILE ELECTROSTIMULATION AND NON-CONTRACTILE NEURAL MODULATION

(75) Inventors: Keith R. Maile, New Brighton, MN (US); Ramprasad Vijayagopal, Shoreview, MN (US); Nicholas J. Stessman, Minneapolis, MN (US); Firmin Musungu, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 118 days.

(21) Appl. No.: 13/099,546

(22) Filed: May 3, 2011

(65) Prior Publication Data

US 2011/0276103 A1    Nov. 10, 2011

Related U.S. Application Data

(60) Provisional application No. 61/332,347, filed on May 7, 2010.

(51) Int. Cl.
*A61N 1/00* (2006.01)

(52) U.S. Cl.
USPC .................................................. 607/9

(58) Field of Classification Search
USPC .............................. 607/9, 2, 59, 119
See application file for complete search history.

(56) References Cited

U.S. PATENT DOCUMENTS

| 5,111,815 | A  | 5/1992  | Mower |
| 5,199,428 | A  | 4/1993  | Obel et al. |
| 5,658,318 | A  | 8/1997  | Stroetmann et al. |
| 6,181,969 | B1 | 1/2001  | Gord |
| 6,199,428 | B1 | 3/2001  | Estevez-Garcia et al. |
| 7,096,064 | B2 | 8/2006  | Deno et al. |
| 7,570,999 | B2 | 8/2009  | Libbus et al. |
| 7,587,238 | B2 | 9/2009  | Moffitt et al. |
| 7,660,628 | B2 | 2/2010  | Libbus et al. |
| 2004/0172075 | A1 | 9/2004  | Shafer et al. |
| 2005/0283197 | A1 | 12/2005 | Daum et al. |
| 2006/0206153 | A1 | 9/2006  | Libbus et al. |
| 2006/0206154 | A1 | 9/2006  | Moffitt et al. |

(Continued)

FOREIGN PATENT DOCUMENTS

WO     WO-2011140022 A2    11/2011
WO     WO-2011140022 A3    11/2011

OTHER PUBLICATIONS

"International Application Serial No. PCT/US2011/034902, International Preliminary Report on Patentability mailed Nov. 22, 2012", 8 pgs.

(Continued)

*Primary Examiner* — George Manuel
*Assistant Examiner* — Robert N Wieland
(74) *Attorney, Agent, or Firm* — Schwegman Lundberg & Woessner, P.A.

(57) ABSTRACT

An apparatus comprises an electrostimulation energy storage capacitor, a circuit path that provides pacing stimulation from the capacitor through the load, a constant current neural stimulation circuit that is switchable into the circuit path to provide neural stimulation through the load and switchable out of the circuit path to provide the pacing stimulation through the load, and a control circuit configured to selectively enable delivery of the pacing stimulation or the constant current neural stimulation.

20 Claims, 9 Drawing Sheets

U.S. PATENT DOCUMENTS

| | | | |
|---|---|---|---|
| 2006/0253157 | A1 | 11/2006 | Libbus et al. |
| 2007/0260283 | A1 | 11/2007 | Li |
| 2007/0260284 | A1 | 11/2007 | Pastore et al. |
| 2008/0058871 | A1* | 3/2008 | Libbus et al. .................... 607/2 |
| 2008/0281372 | A1 | 11/2008 | Libbus et al. |
| 2009/0234406 | A1 | 9/2009 | Shuros et al. |
| 2010/0106231 | A1 | 4/2010 | Torgerson et al. |
| 2011/0288615 | A1* | 11/2011 | Armstrong et al. ............. 607/59 |

OTHER PUBLICATIONS

"International Application Serial No. PCT/US2011/034902, International Search Report mailed Dec. 19, 2011", 3 pgs.

"International Application Serial No. PCT/US2011/034902, Written Opinion mailed Dec. 19, 2011", 7 pgs.

"Japanese Application Serial No. Unknown (N/A), Voluntary Amendment filed Oct. 31, 2012", 12 pgs.

* cited by examiner

OUTPUT CIRCUIT FOR BOTH CARDIAC CONTRACTILE ELECTROSTIMULATION AND NON-CONTRACTILE NEURAL MODULATION

CROSS-REFERENCE TO RELATED APPLICATIONS

This application claims the benefit of U.S. Provisional Application No. 61/332,347, filed on May 7, 2010, under 35 U.S.C. §119(e), which is incorporated herein by reference in its entirety.

BACKGROUND

Implantable medical devices (IMDs) include, among other things, cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural or neuro-stimulation capability. CFM devices typically use pacing output circuits dedicated to provide output voltage pulses, while neural stimulation devices typically use output circuits dedicated to provide constant current.

OVERVIEW

This document discusses examples of techniques for generating and delivering both pacing therapy and neural stimulation therapy. In particular, it relates to devices and methods to deliver the therapies using a single circuit.

In example 1, an apparatus includes an electrostimulation energy storage capacitor, a circuit path that provides pacing stimulation from the capacitor through the load, a constant current neural stimulation circuit that is switchable into the circuit path to provide neural stimulation through the load and switchable out of the circuit path to provide the pacing stimulation through the load, and a control circuit configured to selectively enable delivery of the pacing stimulation or the constant current neural stimulation.

In example 2, the apparatus of example 1 optionally includes a first port configured to be communicatively coupled to an implantable electrode to contact the load and a first switch circuit communicatively coupled to the first port. The constant current neural stimulation circuit optionally includes a constant current source, and the circuit path optionally includes a circuit node connectable to the first port via the first switch circuit. The electrostimulation energy storage capacitor and the constant current source are optionally switchable to the circuit node.

In example 3, the apparatus of any one of examples 1 or 2 optionally includes a second switch circuit communicatively coupled to the control circuit. The constant current source is optionally arranged in series with the electrostimulation energy storage capacitor and the circuit node, and the second switch is optionally configured to bypass the constant current source when delivery of the pacing stimulation is enabled by the control circuit.

In example 4, the apparatus of any one of examples 1-3 optionally includes a recharge capacitor to receive energy from the pacing stimulation and the neural stimulation via the circuit path, and a switch network communicatively coupled to the recharge capacitor. The switch network is optionally configured to alter the circuit path to provide a charge-restoring stimulus from the recharge capacitor through the load, and the charge-restoring stimulus has a polarity opposite to a polarity of one or more of the pacing stimulation and the neural stimulation.

In example 5, the apparatus of any one of examples 1-4 optionally includes a second port configured to be coupled to a second implantable electrode, and the switch network of example 4 optionally includes a third switch communicatively coupled to the circuit node and the first port, and a fourth switch communicatively coupled to the recharge capacitor and the second port. The control circuit is optionally configured to enable the third and fourth switches to direct the pacing stimulation and the neural stimulation from the first port to the second port when the first and second ports are communicatively coupled to the load, and to enable charging of the recharge capacitor using the pacing stimulation and the neural stimulation.

In example 6, the controller circuit of example 5 is optionally configured to enable the fourth switch after delivery of the pacing stimulation and the neural stimulation to provide the charge-restoring stimulus to the second port.

In example 7, the switch network of any one of examples 4-6 is optionally communicatively coupled to the control circuit, and the control circuit is optionally configured to selectively reverse a polarity of one or more of the pacing stimulation, the neural stimulation, and the charge-restoring stimulus.

In example 8, the apparatus of any one of claims 1-7 optionally includes a second port configured to be coupled to a second implantable electrode. The switch network of any one of claims 4-7 optionally includes a fifth switch communicatively coupled to the circuit node and the second port, and a sixth switch communicatively coupled to the first port and the recharge capacitor. The control circuit is optionally configured to enable the fifth and sixth switches to direct the pacing stimulation and the neural stimulation from the second port to the first port when the first and second ports are communicatively coupled to the load, and to enable charging of the recharge capacitor using the pacing stimulation and the neural stimulation.

In example 9, the controller circuit of example 8 is optionally configured to enable the sixth switch after delivery of the pacing stimulation and the neural stimulation to provide the charge-restoring stimulus to the first port.

In example 10, the constant current source of any one of examples 2-9 optionally includes a current mirror that is programmable to provide different amplitudes of constant current, and the programmable current mirror is switchable to the circuit node.

In example 11, the apparatus of claim 1 optionally includes a first port configured to be communicatively coupled to a first implantable electrode to contact the load, and a second port configured to be communicatively coupled to a second implantable electrode to contact the load. The circuit path optionally includes the first port and the second port. The electrostimulation energy storage capacitor is optionally switchable in the circuit path to communicatively couple to the first port. The constant current neural stimulation circuit optionally includes a constant current sink, and the constant current sink is switchable in the circuit path to communicatively couple to the second port.

In example 12, the apparatus of any one of claims 1 or 11 optionally includes a switch circuit communicatively coupled to the control circuit. The constant current sink is optionally arranged in series with the electrostimulation energy storage capacitor, the first port, and the second port. The switch circuit is optionally configured to bypass the constant current sink when the pacing stimulation is enabled by the control circuit.

In example 13, the apparatus of example 12 optionally includes a recharge capacitor communicatively coupled to the switch circuit and configured to receive energy from the pacing stimulation and the neural stimulation via the circuit path. The control circuit is optionally configured to enable the switch circuit to provide a charge-restoring stimulus from the recharge capacitor to the second port and through the load.

In example 14, the constant current neural stimulation circuit of any one of examples 1-13 optionally includes a current mirror that is programmable to provide different amplitudes of constant current.

In example 15, the constant current neural stimulation circuit of any one of examples 1-14 optionally includes a programmable voltage reference circuit, wherein the constant current neural stimulation circuit regulates current according to a programmable voltage reference.

In example 16, the apparatus of any of examples 1-15 optionally includes a capacitive divider circuit configured to generate the programmable voltage reference.

In example 17, the capacitive divider circuit of example 16 optionally includes a capacitive digital-to-analog converter (DAC) circuit, and wherein the voltage reference is programmable according to the capacitive DAC.

In example 18, a method includes delivering pacing stimulation using a circuit path of an electronics unit of an IMD. The circuit path provides the pacing stimulation through a load. The method further includes switching constant current neural stimulation into the circuit path to deliver neural stimulation through the load and switching the constant current neural stimulation out of the circuit path to deliver the pacing stimulation.

In example 19, the method of example 18 optionally includes reversing polarity of the pacing stimulation and the constant current neural stimulation on the circuit path.

In example 20, the method of example 18 or 19 optionally includes delivering the pacing stimulation and the neural stimulation using the circuit path after, and in a direction opposite to, delivery of the pacing stimulation and the constant current neural stimulation in order to dissipate after-potentials resulting from the delivery of the pacing stimulation and the constant current neural stimulation.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses devices and methods for generating and delivering pacing therapy and neural stimulation therapy. Specifically, devices and methods for providing both pacing therapy and neural stimulation therapy via the same circuit are described.

An implantable medical device (IMD) may include one or more of the features, structures, methods, or combinations thereof described herein. For example, a cardiac stimulator may be implemented to include one or more of the advantageous features or processes described below. It is intended that such a stimulator or other implantable or partially implantable device need not include all of the features described herein, but may be implemented to include selected features that provide for unique structures or functionality. Such a device may be implemented to provide a variety of therapeutic or diagnostic functions.

Figure 1:
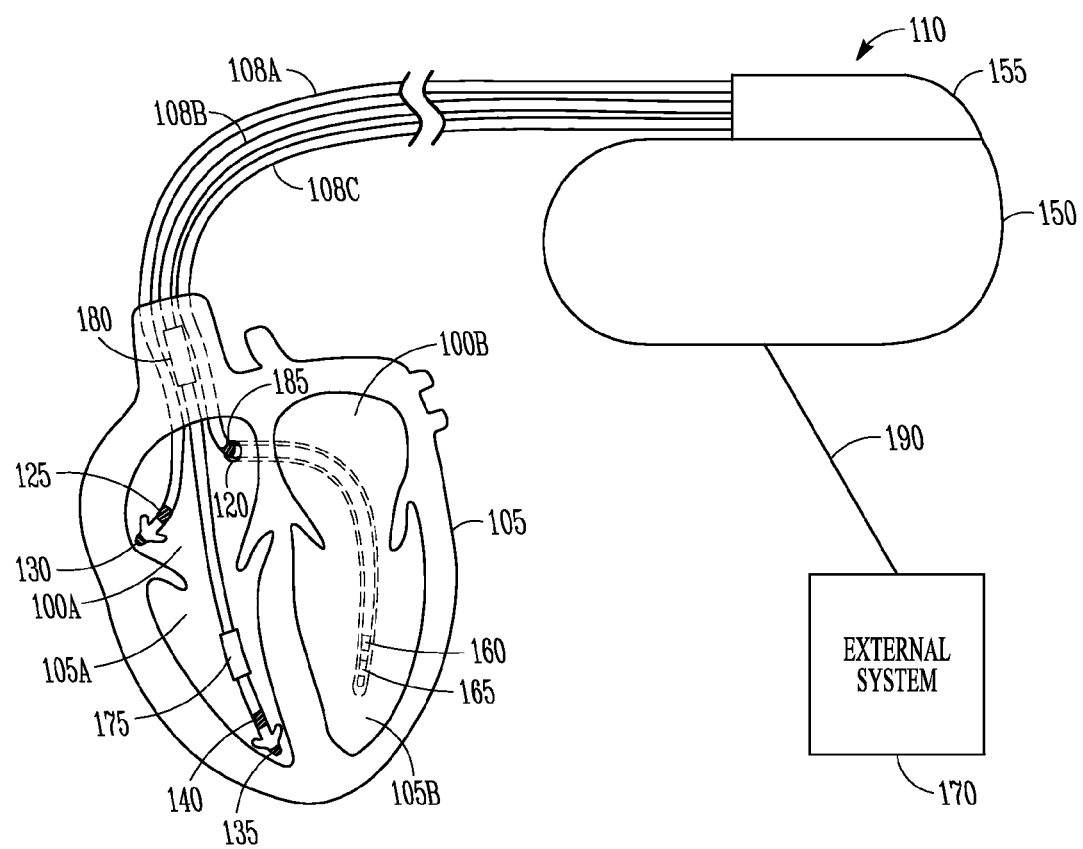
FIG. 1 is an illustration of an example of portions of a system that includes an implantable medical device.

FIG. 1 is an illustration of portions of a system 100 that uses an IMD 110. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 182 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 182.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, the present methods and systems will work in a variety of configurations and with a variety of electrodes. Other forms of electrodes include meshes and patches which may be applied to portions of heart 105 or which may be implanted in other areas of the body to help "steer" electrical currents produced by IMD 110.

An IMD may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

An IMD that delivers neural stimulation therapy can include leads and electrodes designed for placement to provide therapy to specific areas of the nervous system, including the sympathetic nervous system and the parasympathetic nervous system. The sympathetic nervous system is associated with increased blood flow, heart rate, and increased skeletal muscle blood flow. The parasympathetic nervous system is associated with decreased blood pressure, heart rate, and increased digestion.

Stimulating the sympathetic and parasympathetic nervous systems can affect other areas besides heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

In some examples, a neural stimulation device may locally stimulate specific nerve endings in arterial walls rather than stimulate afferent nerve trunks in an effort to stimulate a desired response (e.g. reduced hypertension) while reducing the undesired effects of indiscriminate stimulation of the nervous system. In certain examples, baroreceptor sites in the pulmonary artery are stimulated. In some examples, a neural stimulation device stimulates baroreceptor sites or nerve endings in the aorta and the chambers of the heart, and/or an afferent nerve trunk, such as the vagus, carotid and aortic nerves. In some examples, neural stimulation devices stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Figure 2:
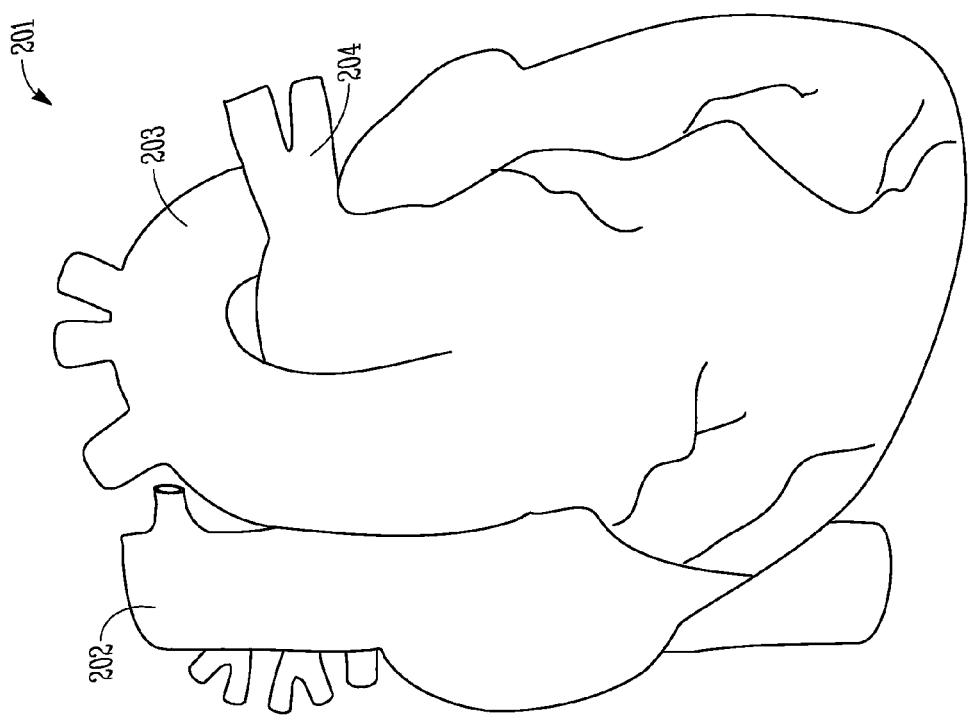
FIG. 2 is an illustration of a heart including the superior vena cava, the aortic arch, and the pulmonary artery.

FIG. 2 illustrates a heart. The heart 201 includes a superior vena cava 202, an aortic arch 203, and a pulmonary artery 204. The pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead described above, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery. Alternatively, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreflex stimulator intravascularly into the pulmonary artery.

Figure 3:
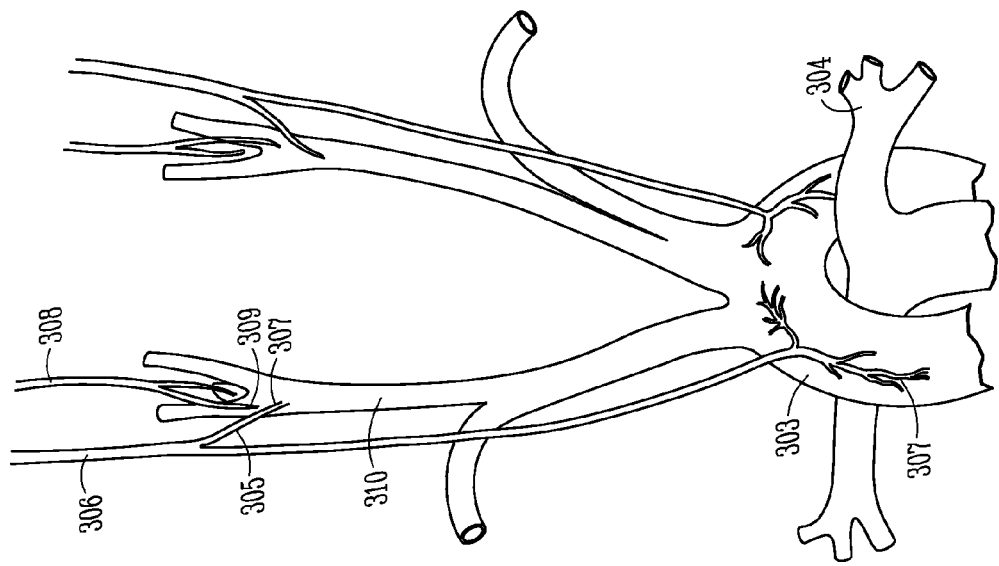
FIG. 3 illustrates baroreceptors in the area of the carotid sinus, aortic arch, and pulmonary artery.

FIG. 3 illustrates baroreceptors in the area of the carotid sinus 305, aortic arch 303, and pulmonary artery 304. The aortic arch 303 and pulmonary artery 304 were previously illustrated with respect to the heart in FIG. 2. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduces pressure. Although not illustrated in the figures, the atrial and ventricular chambers of the heart also include baroreceptors. Cuffs can be placed around afferent nerve trunks, such as the vagal nerve, leading from baroreceptors to vasomotor centers to stimulate the baroreflex. The cuffs can include electrodes for delivering neural stimulation energy. According to various embodiments of the present subject matter, afferent nerve trunks can be stimulated using a cuff or an intravascularly-fed lead positioned in a blood vessel proximate to the afferent nerves.

Pacing therapy includes cardiac contractile electrostimulation. The stimulation is provided as output voltage pulses to cause depolarization of cardiac cells and contraction of the myocardium. Pacing stimulation can be delivered to the heart as pulses of quasi-constant voltage output.

Figure 4:
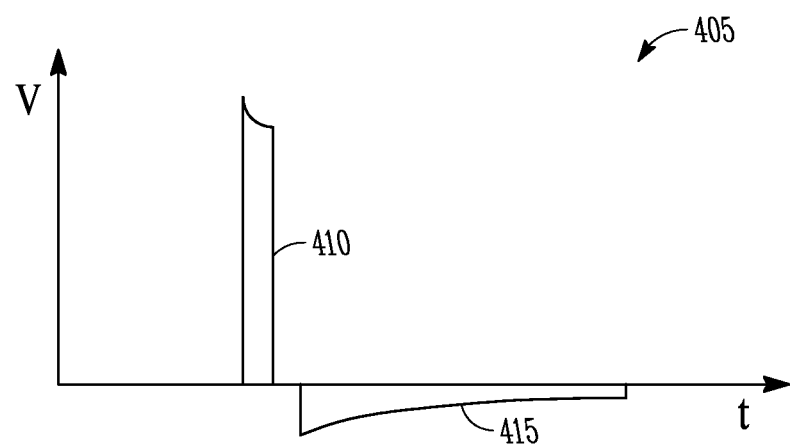
FIG. 4 shows an example of a pacing stimulation pulse.

FIG. 4 shows an example of a pacing stimulation pulse 405. The pacing stimulation pulse 405 can be referred to as quasi-constant because there can be some droop of the amplitude of the pulse. This droop is the result of the RC time constant of the output circuit.

In some examples, the pacing stimulation pulse can involve two portions. The first portion 410 is to initiate a depolarization of myocardial cells. In some examples, the amplitude of the first portion 410 is programmable. The second portion 415 includes a charge-restoring stimulus to dissipate after-potentials resulting from delivery of the first portion 410 of the pacing stimulation. This can reduce the chance of a DC charge accumulating at the electrode/tissue interface. Without the charge-restoring stimulus, the accumulation of charge can reduce the effectiveness of the first portion of the pacing stimulation.

Figure 5:
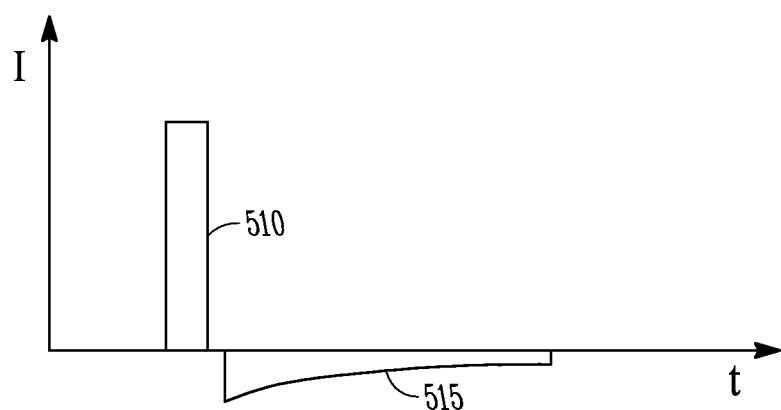
FIG. 5 shows an example of a neural stimulation pulse.

Neural stimulation involves providing energy of constant current to nerves and is not intended to be contractile. FIG. 5 shows an example of a neural stimulation pulse 505. In some examples, the neural stimulation pulse 505 can involve two portions. The first portion 510 is a current pulse of constant current amplitude. The second portion 515 includes a charge-restoring stimulus. In some examples, the amplitude of the first portion 510 is programmable. Nerves can adapt to the stimulation and effectiveness of neural stimulation therapy may diminish over time. The neural stimulation can be modulated to mimic the effects of naturally occurring stimulation and to prevent adaptation of the nerves to the artificial stimulation. For example, the amplitude, frequency, wave morphology, burst frequency and/or duration can be adjusted to abate adaptation.

Figure 6:
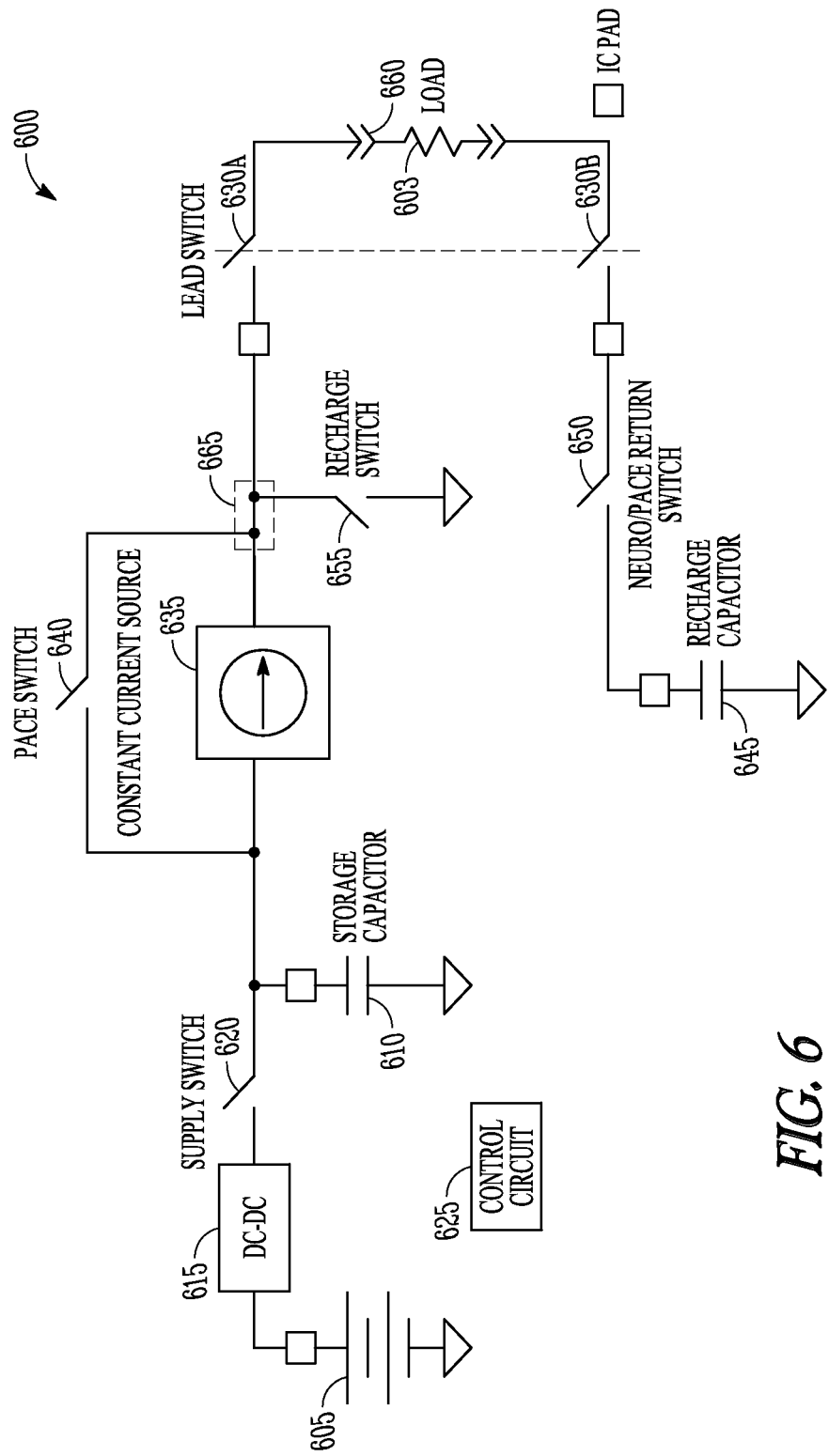
FIGS. 6-10 are diagrams of portions of several examples of a device circuit to provide both cardiac pacing therapy and neural stimulation therapy to a load.

Typical CFM device are not able to provide both CFM pacing therapy and neural stimulation therapy. FIG. 6 is a diagram of portions of an example of a device circuit 600 that provides both cardiac pacing therapy and neural stimulation therapy to a load 603. Examples of the load 603 include, among other things, specific areas of the myocardium and specific areas of the nervous system of a patient or subject.

To provide energy for a therapy, an energy supply 605 (e.g., a battery) can be used to pre-charge an electrostimulation energy storage capacitor 610. In some examples, the circuit 600 includes a DC-DC voltage converter 615 to change a voltage provided to the capacitor 610 via a Supply Switch 620. As shown in FIG. 6, a circuit path provides energy for pacing stimulation from the capacitor 610 through the load 603.

A control circuit 625 provides the timing of the therapy. Examples of a control circuit 625 include a processor (such as a microprocessor, digital signal processor (DSP), or other kind of processor), an application specific integrated circuit (ASIC), and a logic state machine or sequencer to cycle the control circuit through a series of states to perform the functions described. Connections of the control circuit 625 to the circuit path are not shown to simplify the diagram.

The control circuit 625 provides pacing stimulation by pre-charging the capacitor 610 and then electrically connecting the capacitor 610 to the load 603 via electrodes using electrode switches or lead switches 630A, 630B.

The device circuit 600 includes a constant current neural stimulation circuit 635 that is switchable into the circuit path (e.g., by opening pacing switch 640) to provide neural stimulation through the load 603. The constant current neural stimulation circuit 635 is switchable out of the circuit path (e.g., by closing pacing switch 640) to provide the pacing stimulation through the load 603. The control circuit 625 selectively enables delivery of the pacing stimulation or the constant current neural stimulation, such as by changing state of the pacing switch 640. The constant current neural stimulation circuit 635 provides neural stimulation that is independent of the impedance of the load.

In the example of FIG. 6, the constant current neural stimulation circuit 635 includes a constant current source. The device circuit 600 includes a first port 660 in the circuit path. The first port 660 can be communicatively coupled to an implantable electrode (e.g., a lead or can electrode) to contact the load 603. The communicative coupling allows signals such as a therapy stimulus or other stimulus to pass between the first port 660 and the electrode even though there may be intervening circuit or structures between the first port 660 and the electrode. The circuit path includes a circuit node 665 connectable to the first port via a lead switch 630A. The electrostimulation energy storage capacitor 610 and the constant current source 635 are switchable to the circuit node.

Figure 7:
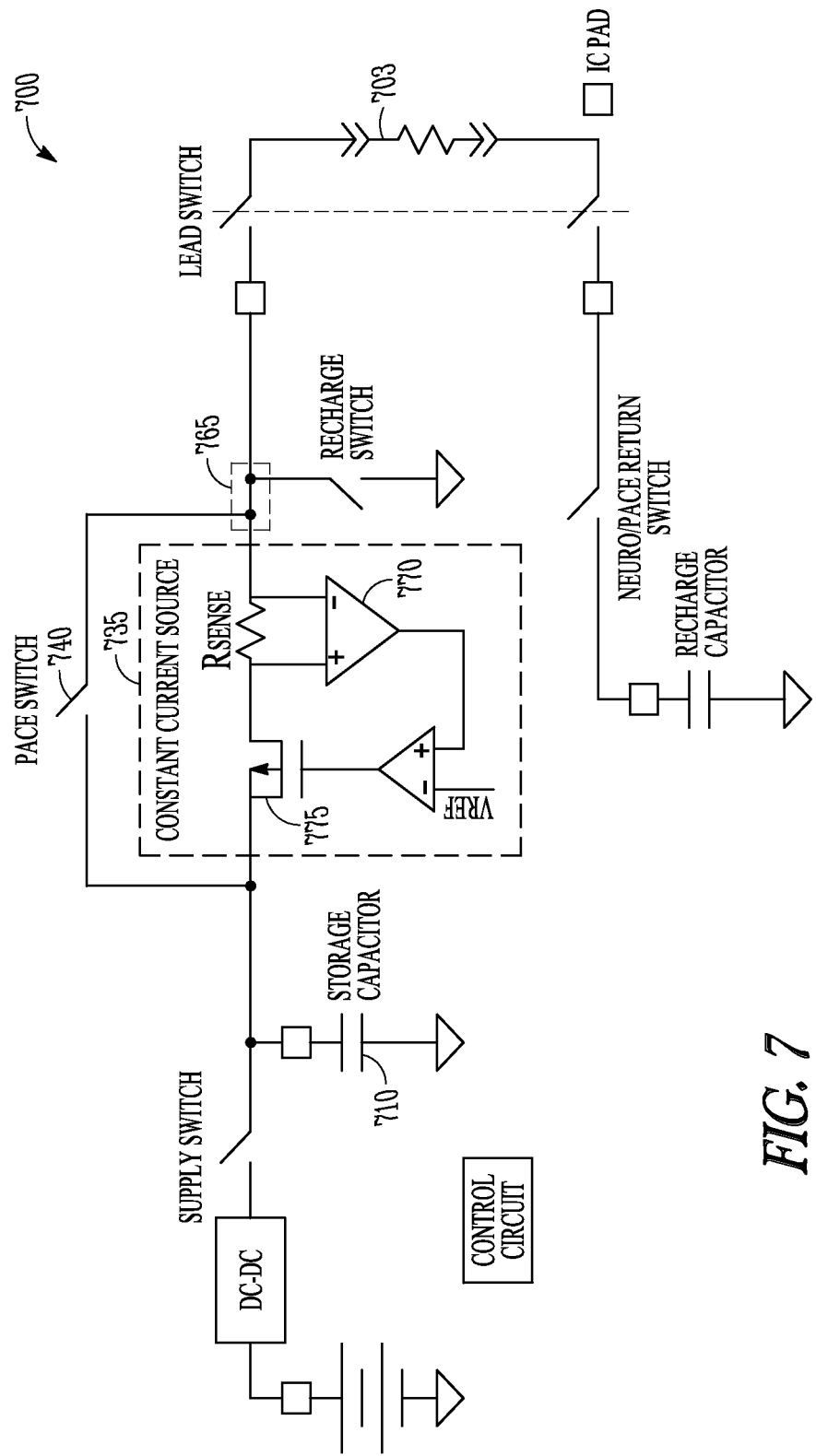

FIG. 7 is a diagram of portions of another example of a device circuit 700 that provides both cardiac pacing therapy and neural stimulation therapy to a load 703. The example shows a more detailed example of a current source. The circuit 700 includes an electrostimulation energy storage capacitor 710. The current source converts current flowing from the capacitor 710 into a current having constant amplitude.

To provide the constant current, sense amplifier 770 senses the voltage across the sense resistor (Rsense), and the source-drain current in field effect transistor (FET) 775 is controlled according to the difference between the Rsense voltage and a voltage reference (Vref). If the first port is to be electrically connected to a lead, the value of Rsense should be selected to be much smaller than the impedance of the lead. The FET 775 should be sized large enough to handle the neural stimulation current.

The circuit 700 also includes a pace switch 740, and a circuit node 765. In some examples, the constant current source 735 is in series with the electrostimulation energy storage capacitor 710 and the circuit node 765. The pace switch 740 bypasses the constant current source 735 when delivery of the pacing stimulation is enabled by the control circuit. Note that the circuits described do not require firmware or software support except for selecting whether to deliver pacing stimulation or neural stimulation.

Returning to FIG. 6, the device circuit 600 includes a recharge capacitor 645 in some examples. The circuit path provides energy to the recharge capacitor 645 from quasi-constant voltage pacing stimulation or constant current neural stimulation through the load 603. In some examples, the circuit path includes return switch 650 to complete the path to the recharge capacitor 645. After delivery of the pacing stimulation or neural stimulation, energy stored on recharge capacitor 645 is used to provide a charge-restoring stimulus to the load such as by activation of return switch 650 and recharge switch 655. Note that the charge-restoring stimulus has a polarity opposite to the polarity of the delivered pacing stimulation or neural stimulation.

Figure 8:
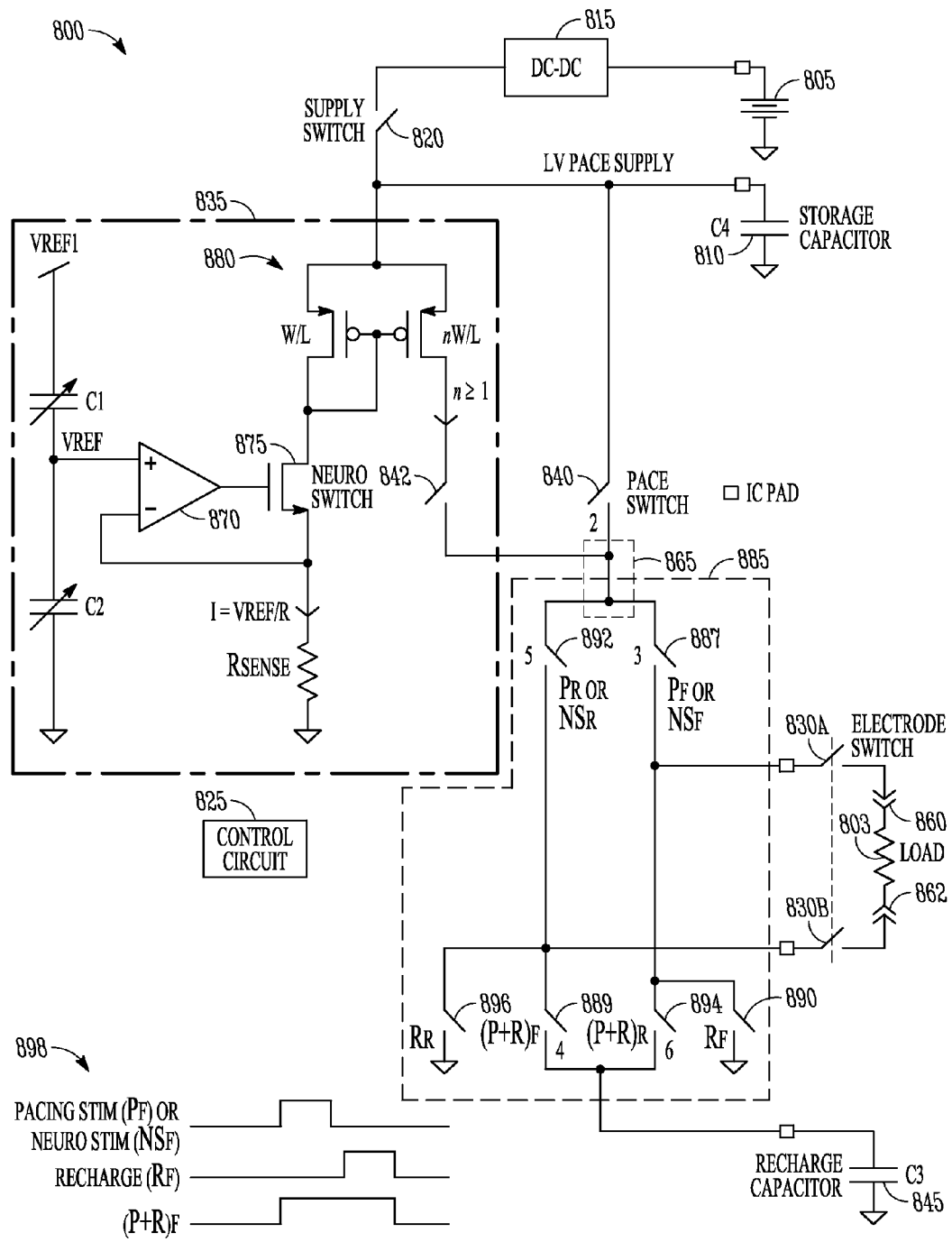

FIG. 8 is a diagram of portions of still another example of a device circuit 800 that provides both cardiac pacing therapy and neural stimulation therapy to a load 803. The circuit 800 includes an energy supply 805 to provide charge to an electrostimulation energy storage capacitor 810 via supply switch 820. A circuit path provides energy for pacing stimulation from the capacitor 810 through the load 803.

The device circuit 800 also includes a constant current neural stimulation circuit 835 that is switchable into the circuit path to provide neural stimulation through the load 803. In this example, the constant current neural stimulation circuit 835 is a constant current source. The current source includes a current mirror 880. The reference current in the current mirror is set by the current in Rsense. Sense amplifier 870 senses the voltage across the sense resistor (Rsense), and the reference current (the source-drain current in transistor 875) is controlled according to I=Vref/Rsense, where Vref is the voltage at the input to the sense amplifier 870. The reference current on the reference leg of the current mirror 880 is then mirrored in the mirror leg(s) of the current mirror and delivered to the load 803. The mirrored current may be switched into circuit node 865 of the circuit path by activating neuro-switch 842 and deactivating pace switch 840.

In some examples, the current source is programmable to provide different amplitudes of constant current. As shown in the Figure, the reference current may be mirrored from 1 to n times, where n is an integer greater than or equal to 1. The neural stimulation current is programmable by activating 1 to n of the mirror legs of the current mirror 880, such as by writing a register using the control circuit 825.

In some examples, the constant current neural stimulation circuit 835 includes a programmable voltage reference circuit. In the Figure, the programmable voltage reference circuit is represented by the capacitive divider circuit that includes the adjustable capacitances C1 and C2. The voltage reference can then be generated according to Vref=[Vref1][Z1/(Z1+Z2)]. The voltage reference is programmable by changing values of the capacitances C1 and C2.

In some examples, the capacitive divider circuit includes a capacitive digital-to-analog converter (DAC) circuit. A DAC register or registers can be written with a digital value by the control circuit 825. Different digital values result in different capacitive ratios to set the value of Vref. The voltage reference Vref is therefore programmable according to the capacitive DAC. A programmable value of Vref provides an additional level of control over the value of constant current provided in the neural stimulation therapy. The combination of the programmable voltage reference and the programmable current mirror provides a wide range of constant current amplitudes which allows accurate control of the current density at the electrode-nerve tissue interface.

In some examples, the device circuit 800 includes a recharge capacitor 845 and a switch network 885 communicatively coupled to the recharge capacitor 845 and the control circuit 825. The recharge capacitor 845 receives energy from the pacing stimulation and the neural stimulation via the circuit path. The switch network 885 alters the circuit path via its switches to provide a charge-restoring stimulus from the recharge capacitor 845 through the load 803. The charge-restoring stimulus has a polarity opposite to a polarity of one or more of the pacing stimulation and the neural stimulation.

The circuit path includes a first port 860 connectable to an implantable electrode. The first port 860 is connectable to circuit node 865 via a first switch (lead switch or electrode switch 830A). The circuit path bypasses the constant current source when a second switch (the pacing switch 840) is active. The circuit path may include a second port 862 connectable to a second implantable electrode.

In some examples, the switch network 885 includes a third switch 887 communicatively coupled to the circuit node 865 and the first port 860 (via electrode switch 830A), and includes a fourth switch 889 communicatively coupled to the recharge capacitor 845 and the second port 862 (via electrode switch 830B). The control circuit 825 enables the third and fourth switches to direct the pacing stimulation and the neural stimulation through the load 803 from the first port 860 to the second port 862 (e.g., a forward direction) when the first and second ports are communicatively coupled to the load 803, and enables charging of the recharge capacitor 845 using the pacing stimulation and the neural stimulation.

To provide a charge-restoring stimulus, the control circuit 825 enables or activates the fourth switch 889 and a forward recharge ($R_F$) switch 890. Note that the charge-restoring stimulus is directed through the load 803 from the second port 862 to the first port 860 and has opposite polarity of the pacing stimulation and the neural stimulation. In certain examples, the first port is connectable to a tip electrode of a bipolar electrode pair and the second port is connectable to ring electrode of the bipolar electrode pair. FIG. 8 includes a timing diagram 898 for the switch activation included in applying pacing stimulation or neural stimulation.

In some examples, the control circuit 825 uses the switch network 885 to change the circuit path to selectively reverse a polarity of one or more of the pacing stimulation, the neural stimulation, and the charge-restoring stimulus. The switch network 885 may include a fifth switch 892 communicatively coupled to the circuit node 865 and the second port 862 (via electrode switch 830B), and a sixth switch 894 communicatively coupled to the first port 860 (via electrode switch 830A) and the recharge capacitor 845. The control circuit 825 enables the fifth and sixth switches to direct the pacing stimulation and the neural stimulation through the load from the second port (862) to the first port (860) when the first and second ports are communicatively coupled to the load 803, and enables charging of the recharge capacitor 845 using the pacing stimulation and the neural stimulation (from the first port 860 through the sixth switch 894).

To provide a charge-restoring stimulus, the control circuit 825 enables the sixth switch 894 and a reverse recharge ($R_R$) switch 890. Note that the charge-restoring stimulus is directed through the load 803 from the first port 860 to the second port 862 and has opposite polarity of the pacing stimulation and the neural stimulation.

Thus far, the example circuits have been described with a constant current source as the current supply providing the constant current neural stimulation therapy. In some examples, a constant current sink provides the constant current.

Figure 9:
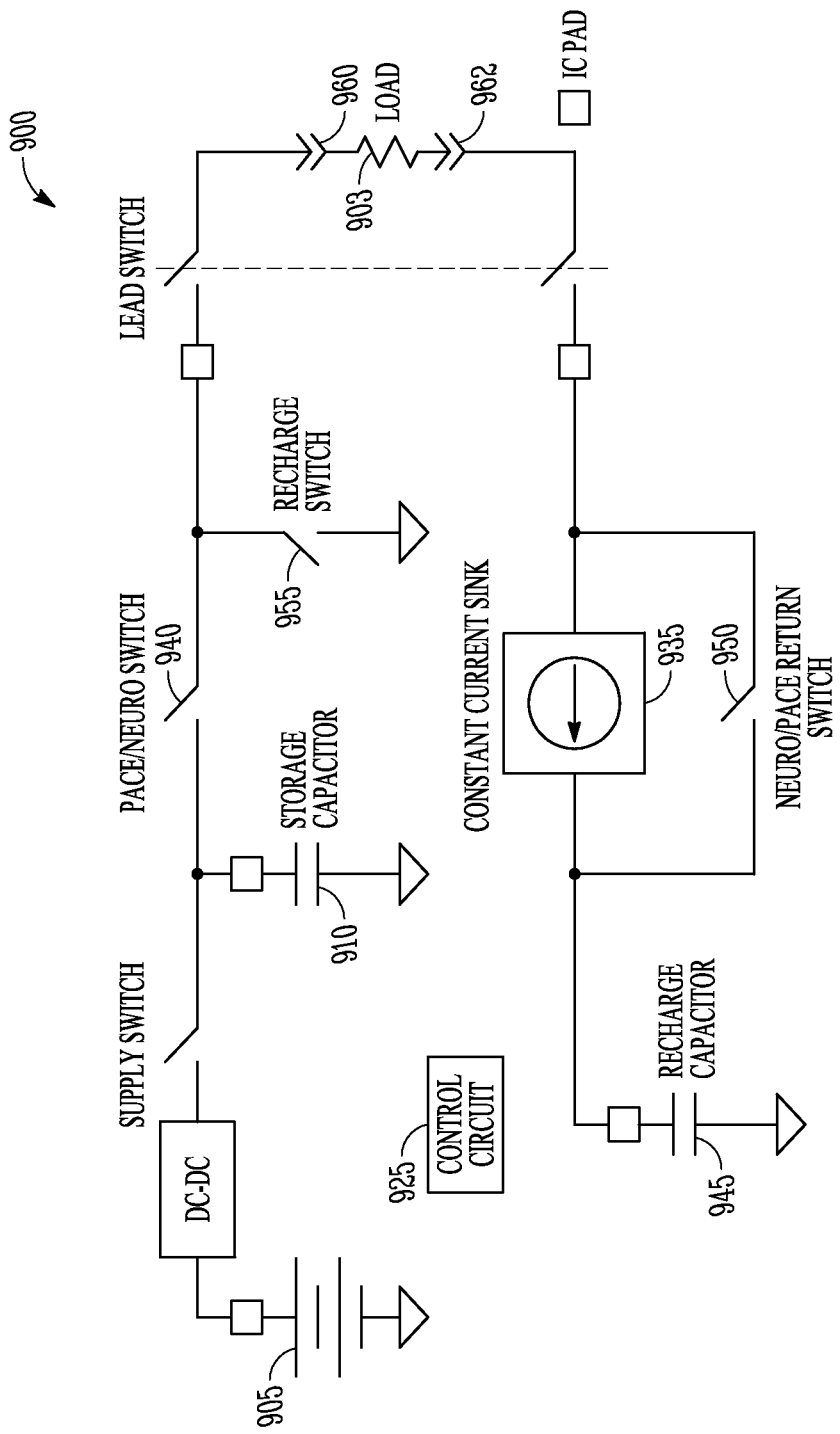

FIG. 9 is a diagram of portions of still another example of a device circuit 900 that provides both cardiac pacing therapy and neural stimulation therapy to a load 903. As in the examples of FIGS. 6-8, an energy supply 905 pre-charges an electrostimulation energy storage capacitor 910. A circuit path provides energy for pacing stimulation and neural stimulation from the capacitor 910 through the load 903. The circuit path includes a first port 960 and a second port 962 connectable to first and second implantable electrodes, and the capacitor 910 is switchable in the circuit path to communicatively couple to the first port 960. The control circuit 925 selectively enables delivery of the pacing stimulation or the constant current neural stimulation, such as by changing state of the pacing/neuro switch 940. The capacitor 910 can be switchable to the circuit path by closing the pacing/neuro switch 940.

The device circuit 900 includes a constant current neural stimulation circuit 935, but in this example the constant current neural stimulation circuit 935 includes a constant current sink. The constant current sink is arranged in series with the electrostimulation energy storage capacitor 910, the first port 960, and the second port 962. The device circuit 900 includes a return switch 950. The constant current sink is switchable into the circuit path by disabling or deactivating return switch 950 to communicatively couple the constant current sink to the second port 962. The current sink is switchable out of the circuit path by activating the return switch 950 to bypass the constant current sink when the pacing stimulation is enabled by the control circuit 925.

In some examples, the device circuit 900 includes a recharge capacitor 945 communicatively coupled to the return switch 950 and a recharge switch 955. The recharge capacitor 945 receives energy from the pacing stimulation and the neural stimulation via the circuit path. The control circuit 925 enables the return switch 950 and the recharge switch 955 to provide a charge-restoring stimulus from the recharge capacitor 945 to the second port 962 and through the load 903.

Figure 10:
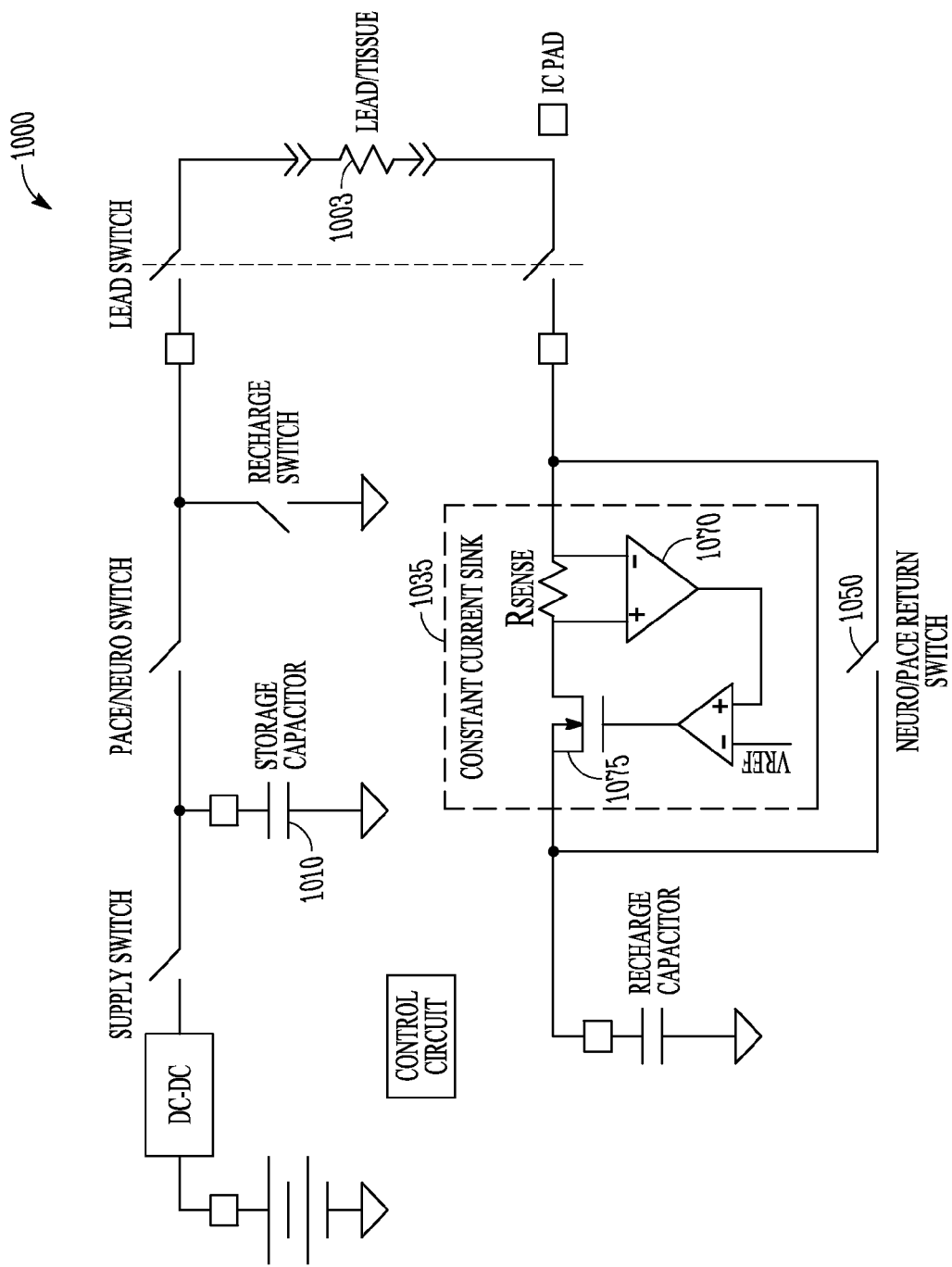

FIG. 10 is a diagram of portions of another example of a device circuit 1000 that provides both cardiac pacing therapy and neural stimulation therapy to a load 1003. The example shows a more detailed example of a current sink. The current sink converts current flowing from the capacitor 1010 and through the load 1003 into a current having constant amplitude. As in the constant current neural stimulation circuit of FIG. 7, sense amplifier 1070 senses the voltage across the sense resistor (Rsense), and the source-drain current in transistor 1075 is controlled according to the difference between the Rsense voltage and a voltage reference (Vref). In some examples, the current sink includes a current mirror that is programmable to provide different amplitudes of constant current. In some examples, the voltage reference is programmable. The return switch 1050 bypasses the constant current sink 1035 when delivery of the pacing stimulation is enabled by the control circuit 1025.

In some examples, a device can be configured for pacing stimulation only or for neural stimulation only. In some examples, a device can include multiple device circuits to provide pacing stimulation and neural stimulation. Some of the device circuits can be configured to deliver pacing stimulation while other can be configured to provide neural stimulation. This allows flexibility in the device after it is manufactured. The device can be designed with N stimulation circuit paths, where N is an integer. Based on the end application, some or all of the N circuit paths can be configured for pacing stimulation, some or all of the N circuit paths can be configured for neural stimulation, or some or all of the N circuit paths can be configured for a combination of pacing stimulation and neural stimulation.

Figure 11:
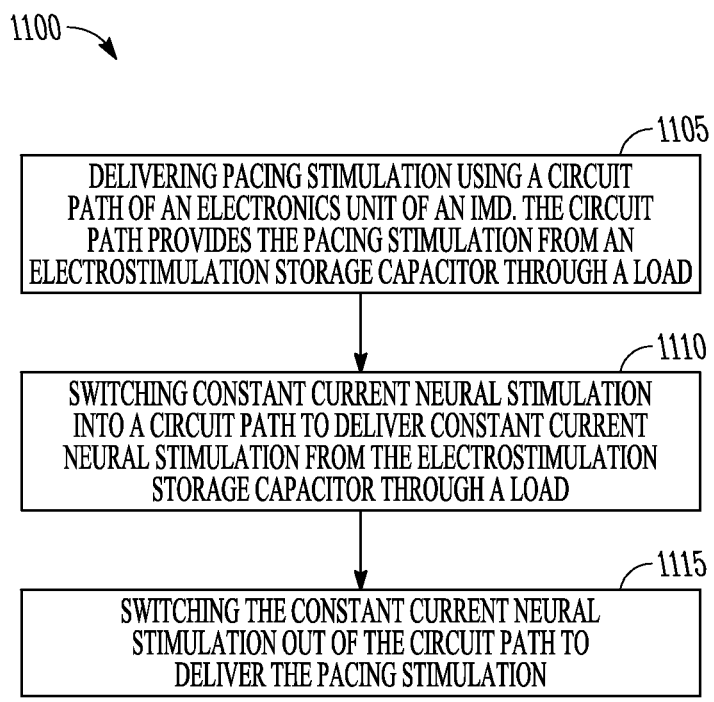
FIG. 11 shows a flow diagram of an example of a method for providing both cardiac pacing therapy and neural stimulation therapy to a load.

FIG. 11 shows a flow diagram of an example of a method 1100 for providing both cardiac pacing therapy and neural stimulation therapy to a load such as areas of the myocardium and areas of the nervous system of a patient or subject.

At block 1105, pacing stimulation is delivered using a circuit path of an electronics unit of an implantable medical device (IMD). The circuit path provides the pacing stimulation from an electrostimulation storage capacitor through a load. The electrostimulation storage capacitor is charged from an energy supply, such as a battery for example, to provide energy for the pacing stimulation. In some examples, the pacing stimulation is quasi-constant voltage stimulation.

At block 1110, constant current neural stimulation is switched into the circuit path to deliver constant current neural stimulation from the electrostimulation storage capacitor through the load. In some examples, the constant current neural stimulation is generated using a constant current source. In some examples, a constant current sink is switched into the circuit path to generate the constant current neural stimulation. The current source or current sink regulates the current discharged from the capacitor to a constant level or amplitude.

At block 1115, the constant current neural stimulation is switched out of the circuit path to deliver the pacing stimulation through the load.

In some examples, the method 1100 includes reversing polarity of the pacing stimulation and the constant current neural stimulation on the circuit path. In certain examples, the polarity is reversed using a switch network to alter the circuit path. In some examples, the method 1100 includes delivering the pacing stimulation and the neural stimulation using the circuit path after, and in a direction opposite to, delivery of the pacing stimulation and the constant current neural stimulation. This energy having opposite polarity of the therapy dissipates after-potentials resulting from the delivery of the pacing stimulation and the constant current neural stimulation.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus for delivering both cardiac pacing therapy and neural stimulation therapy to a load, the apparatus comprising:
    an electrostimulation energy storage capacitor;
    a circuit path that provides pacing stimulation from the capacitor through the load;
    a constant current neural stimulation circuit that is switchable into the circuit path in series with the capacitor and the load to provide neural stimulation from the capacitor through the load and switchable out of the circuit path to provide the pacing stimulation through the load; and
    a control circuit configured to selectively enable delivery of the pacing stimulation or the constant current neural stimulation.

2. The apparatus of claim 1, including:
    a first port configured to be communicatively coupled to an implantable electrode to contact the load; and
    a first switch circuit communicatively coupled to the first port;
    wherein the constant current neural stimulation circuit includes a constant current source, and
    wherein the circuit path includes a circuit node connectable to the first port via the first switch circuit, and wherein the electrostimulation energy storage capacitor and the constant current source are switchable to the circuit node.

3. The apparatus of claim 2, including:
    a second switch circuit communicatively coupled to the control circuit,
    wherein the constant current source is arranged in series with the electrostimulation energy storage capacitor and the circuit node, and
    wherein the second switch is configured to bypass the constant current source when delivery of the pacing stimulation is enabled by the control circuit.

4. The apparatus of claim 2, including:
    a recharge capacitor to receive energy from the pacing stimulation and the neural stimulation via the circuit path; and
    a switch network communicatively coupled to the recharge capacitor, wherein the switch network is configured to alter the circuit path to provide a charge-restoring stimulus from the recharge capacitor through the load, wherein the charge-restoring stimulus has a polarity opposite to a polarity of one or more of the pacing stimulation and the neural stimulation.

5. The apparatus of claim 4, including:
    a second port configured to be coupled to a second implantable electrode;
    wherein the switch network includes:
        a third switch communicatively coupled to the circuit node and the first port; and
        a fourth switch communicatively coupled to the recharge capacitor and the second port,
    wherein the control circuit is configured to enable the third and fourth switches to direct the pacing stimulation and the neural stimulation from the first port to the second port when the first and second ports are communicatively coupled to the load, and to enable charging of the recharge capacitor using the pacing stimulation and the neural stimulation.

6. The apparatus of claim 5, wherein the controller circuit is configured to enable the fourth switch after delivery of the pacing stimulation and the neural stimulation to provide the charge-restoring stimulus to the second port.

7. The apparatus of claim 4, wherein the switch network is communicatively coupled to the control circuit, and wherein the control circuit is configured to selectively reverse a polarity of one or more of the pacing stimulation, the neural stimulation, and the charge-restoring stimulus.

8. The apparatus of claim 7, including:
    a second port configured to be coupled to a second implantable electrode, and
    wherein the switch network includes:
        a fifth switch communicatively coupled to the circuit node and the second port; and
        a sixth switch communicatively coupled to the first port and the recharge capacitor,
    wherein the control circuit is configured to enable the fifth and sixth switches to direct the pacing stimulation and the neural stimulation from the second port to the first port when the first and second ports are communicatively coupled to the load, and to enable charging of the recharge capacitor using the pacing stimulation and the neural stimulation.

9. The apparatus of claim 8, wherein the controller circuit is configured to enable the sixth switch after delivery of the pacing stimulation and the neural stimulation to provide the charge-restoring stimulus to the first port.

10. The apparatus of claim 2, wherein the constant current source includes a current mirror that is programmable to provide different amplitudes of constant current, and wherein the programmable current mirror is switchable to the circuit node.

11. The apparatus of claim 1, including:
a first port configured to be communicatively coupled to a first implantable electrode to contact the load; and
a second port configured to be communicatively coupled to a second implantable electrode to contact the load,
wherein the circuit path includes the first port and the second port,
wherein the electrostimulation energy storage capacitor is switchable in the circuit path to communicatively couple to the first port,
wherein the constant current neural stimulation circuit includes a constant current sink, and
wherein the constant current sink is switchable in the circuit path to communicatively couple to the second port.

12. The apparatus of claim 11, including:
a switch circuit communicatively coupled to the control circuit,
wherein the constant current sink is arranged in series with the electrostimulation energy storage capacitor, the first port, and the second port, and
wherein the switch circuit is configured to bypass the constant current sink when the pacing stimulation is enabled by the control circuit.

13. The apparatus of claim 12, including:
a recharge capacitor communicatively coupled to the switch circuit and configured to receive energy from the pacing stimulation and the neural stimulation via the circuit path, and
wherein control circuit is configured to enable the switch circuit to provide a charge-restoring stimulus from the recharge capacitor to the second port and through the load.

14. The apparatus of claim 1, wherein the constant current neural stimulation circuit includes a current mirror that is programmable to provide different amplitudes of constant current.

15. The apparatus of claim 14, wherein the constant current neural stimulation circuit includes a programmable voltage reference circuit, wherein the constant current neural stimulation circuit regulates current according to a programmable voltage reference.

16. The apparatus of claim 15, including a capacitive divider circuit configured to generate the programmable voltage reference.

17. The apparatus of claim 16, wherein the capacitive divider circuit includes a capacitive digital-to-analog converter (DAC) circuit, and wherein the voltage reference is programmable according to the capacitive DAC.

18. A method comprising:
delivering pacing stimulation using a circuit path of an electronics unit of an implantable medical device (IMD), wherein the circuit path provides the pacing stimulation from an electrostimulation energy storage capacitor through a load;
switching constant current neural stimulation into the circuit path in series with the capacitor and the load to deliver neural stimulation from the capacitor through the load; and
switching the constant current neural stimulation out of the circuit path to deliver the pacing stimulation.

19. The method of claim 18, including reversing polarity of the pacing stimulation and the constant current neural stimulation on the circuit path.

20. The method of claim 18, including delivering the pacing stimulation and the neural stimulation using the circuit path after, and in a direction opposite to, delivery of the pacing stimulation and the constant current neural stimulation to dissipate after-potentials resulting from the delivery of the pacing stimulation and the constant current neural stimulation.

* * * * *